United States Patent [19]
Fortier

[11] Patent Number: 6,106,539
[45] Date of Patent: *Aug. 22, 2000

[54] TROCAR WITH REMOVABLE, REPLACEABLE TIP

[75] Inventor: Richard C. Fortier, Concord, Mass.

[73] Assignee: NeoSurg Technologies, Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 09/060,640

[22] Filed: Apr. 15, 1998

[51] Int. Cl.[7] .................................................. A61B 17/34
[52] U.S. Cl. ..................................... 606/185; 604/164.06
[58] Field of Search ........................... 606/185; 604/164, 604/164.01, 164.06; 30/340, 329; 81/489; 16/422, 426, 427

[56] References Cited

U.S. PATENT DOCUMENTS

| | | |
|---|---|---|
| 649,493 | 5/1900 | Stohmann et al. . |
| 3,187,431 | 6/1965 | Mattes ........................................ 606/167 |
| 4,254,762 | 3/1981 | Yoon . |
| 4,535,773 | 8/1985 | Yoon . |
| 4,601,710 | 7/1986 | Moll . |
| 4,654,030 | 3/1987 | Moll et al. . |
| 4,911,575 | 3/1990 | Tidwell ........................................ 16/426 |
| 4,931,042 | 6/1990 | Holmes et al. . |
| 4,985,035 | 1/1991 | Torre ........................................ 606/167 |
| 5,030,206 | 7/1991 | Lander . |
| 5,116,353 | 5/1992 | Green . |
| 5,256,149 | 10/1993 | Banik et al. . |
| 5,330,493 | 7/1994 | Haining ........................................ 606/167 |
| 5,342,379 | 8/1994 | Volinsky ........................................ 606/167 |
| 5,387,197 | 2/1995 | Smith et al. . |
| 5,405,328 | 4/1995 | Vidal et al. . |
| 5,486,190 | 1/1996 | Green . |
| 5,507,774 | 4/1996 | Holmes et al. ........................................ 606/205 |
| 5,522,833 | 6/1996 | Stephens et al. . |
| 5,554,137 | 9/1996 | Young et al. . |
| 5,591,190 | 1/1997 | Yoon . |
| 5,609,604 | 3/1997 | Schwemberger et al. ........................................ 606/185 |
| 5,664,792 | 9/1997 | Tseng ........................................ 16/422 |
| 5,676,681 | 10/1997 | Yoon . |
| 5,676,683 | 10/1997 | Yoon . |
| 5,686,682 | 11/1997 | Yoon . |
| 5,688,286 | 11/1997 | Yoon . |
| 5,697,947 | 12/1997 | Wolf et al. . |
| 5,810,863 | 9/1998 | Wolf et al. ........................................ 606/185 |

FOREIGN PATENT DOCUMENTS

0078358  11/1982  European Pat. Off. ............. 16/114 R

*Primary Examiner*—Michael H. Thaler
*Attorney, Agent, or Firm*—Iandiorio & Teska

[57] ABSTRACT

A trocar obturator having a removable replaceable tip includes an obturator tip having a sharpened distal end and a first engagement device on its proximal end; an obturator shaft having a second engagement device on its distal end for lockingly engaging the first engagement device and securing the tip and shaft together; one of the engagement devices borne by one of the tips and shafts includes a flexible member biased to engage the engagement devices; there are access means for flexing the flexible member against its bias to disengage the engagement devices to release the tip and shaft.

28 Claims, 7 Drawing Sheets

TROCAR WITH REMOVABLE, REPLACEABLE TIP

FIELD OF INVENTION

This invention relates to an improved obturator having a removable, replaceable tip and more particularly to such a removable, replaceable tip which flexibly engages and releases the obturator tip and shaft.

BACKGROUND OF INVENTION

Conventional trocars use an obturator with a sharp metal tip to penetrate a body cavity in surgical procedures. After each use the obturator must be sterilized and eventually the tip dulls and must be re-sharpened by machining. These obturators are expensive and adding to their effective cost is the cost of sharpening, sterilizing and the loss of use during those procedures. Some trocars including housing, handle, cannula and obturator are made to be disposable: they are made to be used once and discarded with no need for resharpening or sterilizing but their initial cost is quite high. Some trocar obturators are made with a removable metal tip so that tips of different cutting configurations can be used by simple removal and replacement of them from the obturator shaft. But these tips, too, are expensive and must be regularly sterilized and periodically re-sharpened.

SUMMARY OF INVENTION: I

It is therefore an object of this invention to provide an improved obturator having a removable, replaceable tip.

It is a further object of this invention to provide such an obturator which is disposable after a single use.

It is a further object of this invention to provide such an obturator which is inexpensive and easy to install and removal.

It is a further object of this invention to provide such an obturator which is always at peak sharpness and sterile and involves no re-sharpening or sterilization.

It is a further object of this invention to provide such an obturator which sensibly indicates when the tip is seated in the shaft.

The invention results from the realization that a truly cost effective, disposable obturator can be achieved with a separable tip and shaft which have means for properly orienting them and releasably engaging and disengaging them using a flexible member on one bearing a detent which engages with a stop on the other under the bias of the flexible member to secure the tip and shaft which can easily be disengaged by moving the flexible member against its bias to release the detent from the stop and free the tip from the shaft.

This invention features a trocar obturator having a removable replaceable tip including an obturator tip having a sharpened distal end and a first engagement device on its proximal end. There is an obturator shaft having a second engagement device on its distal end for lockingly engaging the first engagement device and securing the tip and shaft together. One of the engagement devices borne by one of the tips and shafts includes a flexible member biased to engage the engagement devices. There are access means for flexing the flexible member against its bias to disengage the engagement devices to release the tip and shaft.

In a preferred embodiment there may be alignment means for defining orientation of the tip and shaft. The alignment means may include a salient portion on one of the tip and shaft and a mating recess on the other. One of the engagement devices on one of the tips and shafts may be asymmetrical in shape and the alignment means may include a conforming guide recess on the other of the tip and shaft for orienting the tip and shaft. The tip may include a circumferential removal groove. The groove may have a circular shape or a polygonal shape such as a square. There may be an indicator surface on one of the tips and shafts and a cover member on the other for covering the indicator surface when the tip and shaft are engaged. The indicator surface may include a contrasting color region. The flexible member may snap the engagement devices together to make an audible indication that the tip and shaft are secured. The tip may be made of plastic such as polycarbonate, ABS, or polysulfone. One of the engagement devices may include at least one flexible leg with a detent and the other engagement device may include a stop means for engaging the detent. The flexible leg may be included on the first engagement device on the tip and the stop means may be on the second engagement device on the shaft. Or the flexible leg may be on the second engagement device on the shaft and the stop means may be on the first engagement device on the tip. The stop means may include a stop recess for receiving the detent or it may include a stop shoulder for abutting the detent. The access means may include a port for manipulating the flexible leg and it may be on the shaft or the tip. The access means may include a resilient tab interconnected with the flexible leg for flexing the leg against its bias to release the tip and shaft. The stop means may include a peripheral slot.

The invention also features a trocar obturator having a removable replaceable tip including an obturator tip having a sharpened distal end and a flexible leg extending from the proximal end and having a detent thereon. An obturator shaft has a stop means for engaging the detent. The flexible leg is biased to engage the detent and stop means to secure the tip and shaft. An access port is provided for moving the leg to overcome its bias, disengage the detent and stop means and release the tip and shaft.

In a preferred embodiment the stop means may include a stop recess for receiving the detent or a stop shoulder for abutting the detent. The access port may be in the shaft and the stop recess may form a part of the port.

This invention also features a trocar obturator having a removable replaceable tip including an obturator tip having a sharpened distal end, an obturator shaft, and engaging means for releasably securing the tip and shaft including a flexible leg having a detent on one of the tip and shaft and stop means on the other for engaging the detent, the flexible leg being biased to engage the detent and step means and secure the tip and shaft. There are access means for moving the leg to overcome its bias, disengage the detent and stop means and release the tip and shaft.

In a preferred embodiment the flexible leg may be on the tip and the stop means may be on the shaft, or the flexible leg may be on the shaft and the stop means on the tip.

DISCLOSURE OF PREFERRED EMBODIMENT

Other objects, features and advantages will occur to those skilled in the art from the following description of a preferred embodiment and the accompanying drawings, in which.

Figure 1:
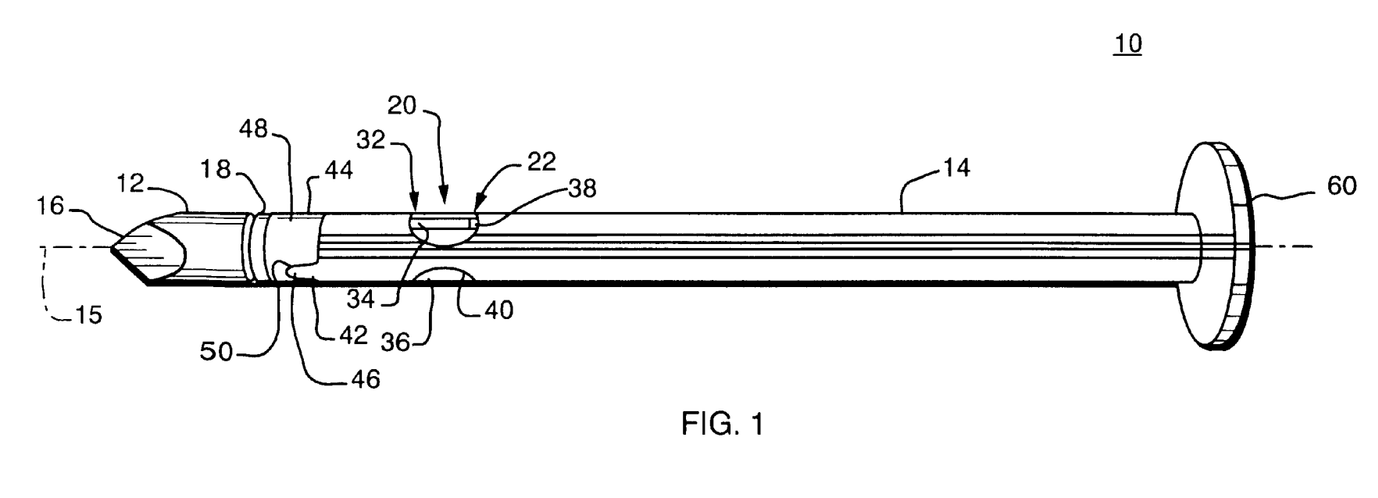
FIG. 1 is a three-dimensional view of a trocar obturator including a removable replaceable tip according to this invention.

There is shown in FIG. 1 a trocar obturator 10 according to this invention including an obturator tip 12 and shaft 14 with a longitudinal axis 15. Tip 12 includes a sharpened distal end 16 and a removal groove 18 for receiving, for example, forceps, to remove tip 12 from shaft 14. Referring to FIGS. 1, 2, 3 and 4, it can be seen that there are engagement means 20 which include an engagement device 22 on tip 12 comprised of a pair of flexible legs 24, 26 having detents 28 and 30. There is also an engagement device 32 on shaft 14 which includes the stop means formed by the stop recesses 34 and 36 that form a part of the oval ports 38 and 40 that constitute the access means by which the fingers of a surgeon can reach and squeeze legs 24 and 26 to move detents 28 and 30 out of contact with stop recesses 34 and 36 in order to release tip 12 from shaft 14. Flexible legs 24 and 26 have a sufficient bias to maintain detents 28 and 30 in contact with stop recesses 34 and 36 and to provide a snap fit which makes a clicking noise when tip 12 is inserted and seated properly in shaft 14 so the surgeon has an audible confirmation that the shaft and tip are locked together. In order to compel the tip 12 to be inserted in shaft 14 so that legs 24 and 26 align with access ports 38 and 40, alignment means 42 consisting of tabs 44 and 46 extending saliently from shaft 14 and recesses 48 and 50 on tip 12 are provided. A handle or hub 60 is provided on the proximal end of shaft 14 to be used to apply pressure to push the sharp end 16 of tip 12 through the body tissue. Shaft 14 is hollow, at least at its distal end to provide for access ports 38 and 40 and permit the legs 24 and 26 of tip 12 to be inserted. To provide for strength, sharp cutting edges and the snap fitting action and sound, the trocar may be made of a metal or of a plastic such as of polycarbonate, ABS, polysulfone.

Figure 2:
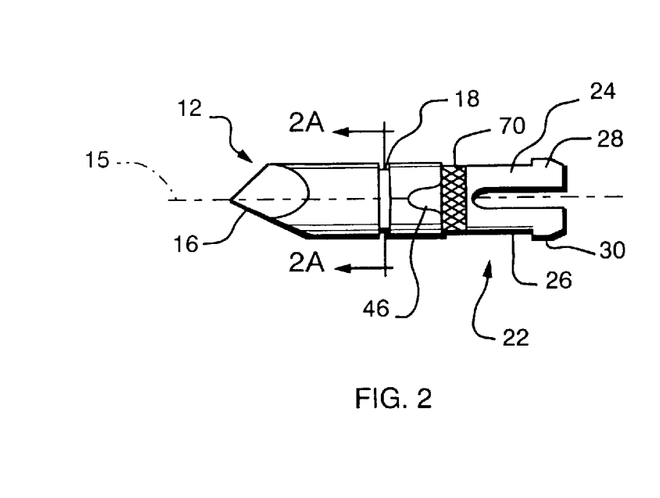
FIG. 2 is an enlarged detail view of the obturator tip of FIG. 1.
Figure 3:
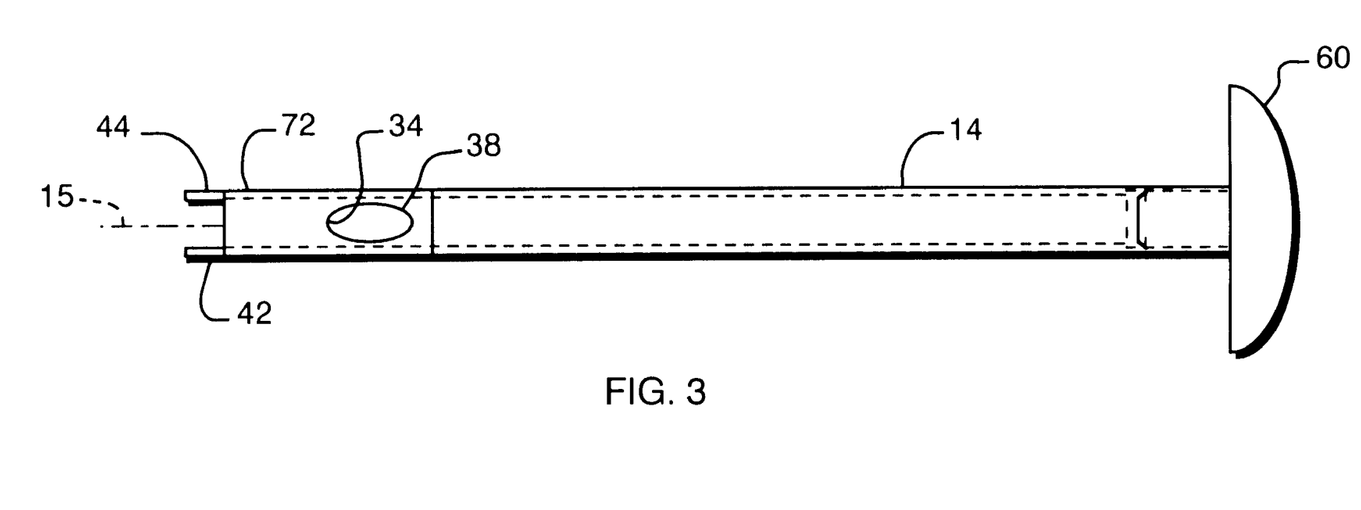
FIG. 3 is a enlarged detailed plan view of the obturator shaft of FIG. 1.
Figure 4:
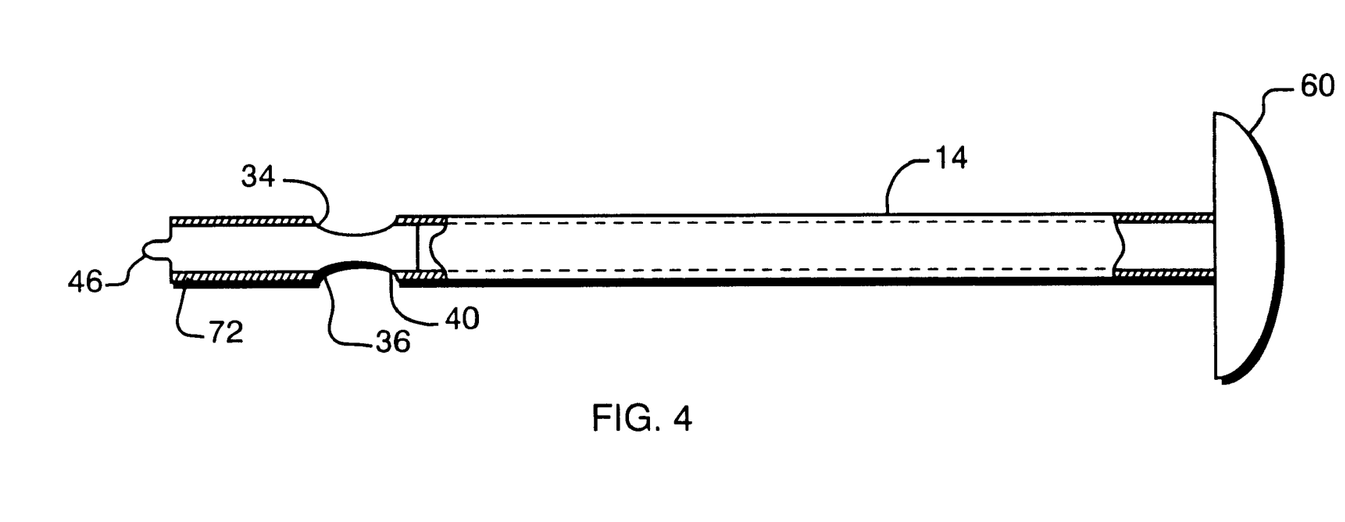
FIG. 4 is an enlarged detailed elevational view of the obturator shaft of FIG. 1.

Visual indicia may be provided in the form of a contrasting color or texture or pattern 70, FIG. 2, which will be covered by cover portion 72, FIGS. 3 and 4, of shaft 14 when tip 12 is properly secured in shaft 14 so the surgeon will have another confirmation that the obturator is properly and safely assembled.

In operation, tip 12 is inserted in shaft 14 by simply pressing the ends of legs 24 and 26 against the cover portion 72 of shaft 14. Legs 24 and 26, being flexible, will flex inward so that detents 28 and 30 will pass under the cover portion and will spring out in ports 38 and 40 making a clicking sound when detents 28 and 30 spring into position at stop recesses 34 and 36. At this point the color band 70 will no longer be visible as it is hidden by the cover portion 72. When the surgical procedure is finished and it is desired to remove tip 12, tip 12 can be gripped by fingers or by a tool such as a forcep which would engage with groove 18 and then the surgeon may place a thumb and forefinger over access ports 38 and 40, depressing legs 24 and 26 so that detents 28 and 30 disengage from stop recesses 34 and 36.

Figure 2A:
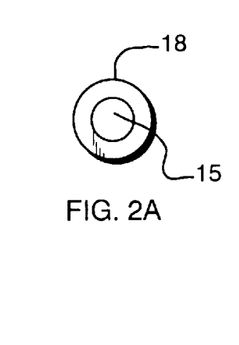
FIG. 2A is a cross-sectional view taken along lines 2A—2A of FIG. 2 showing a groove which has a circular shape.
Figure 2B:
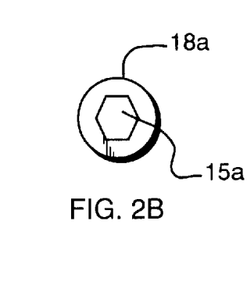
FIG. 2B is a view similar to FIG. 2A in which the groove has a polygonal shape.
Figure 2C:
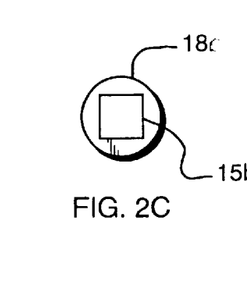
FIG. 2C is a view similar to FIGS. 2A and 2B wherein the groove has a square shape.

Groove 18 has a circular shape or circumference as shown in FIG. 2A, but it may as well have a polygonal shape such as hexagonal shape 18a, FIG. 2B, or square shape 18b, FIG. 2C, to better receive a wrench-like conformation or forceps.

Figure 5:
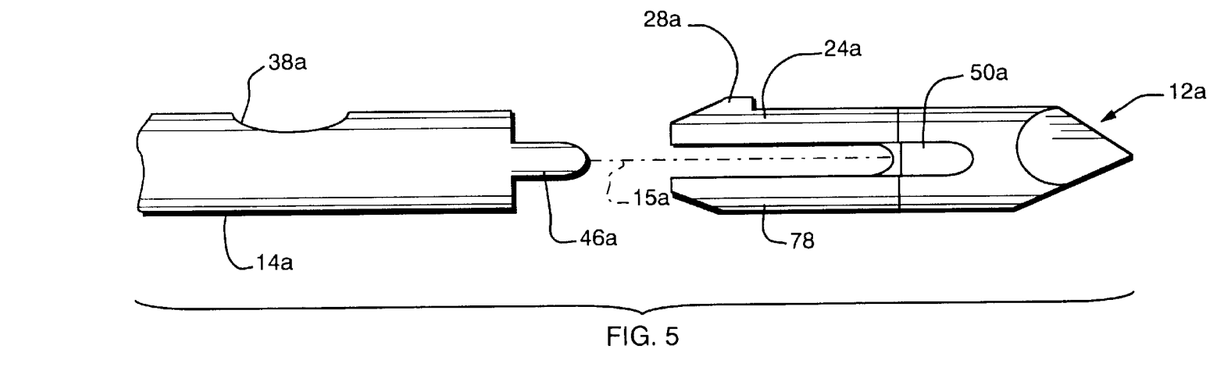
FIG. 5 is a view similar to FIG. 2 wherein there is but one flexible leg, one detent and one access hole.
Figure 6:
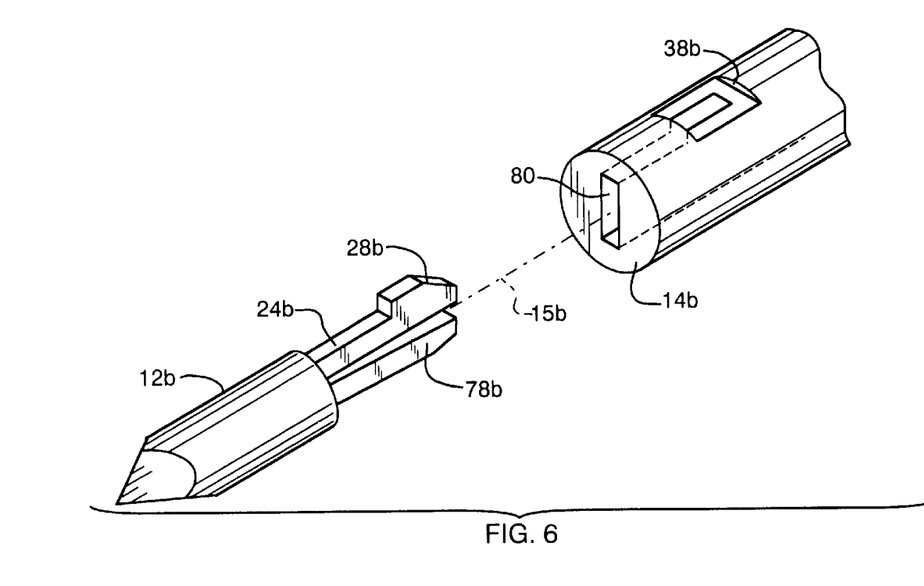
FIG. 6 is a three-dimensional view of the tip of FIG. 5 showing an asymmetric slot in the shaft for definitively orienting the tip and shaft assembly.

Although in FIGS. 1–4 tip 12 is shown with a pair of flexible legs with detents and a pair of access ports, as well as a pair of alignment tabs these are not necessary limitations of the invention. For as shown in FIG. 5, tip 12a may include a single recess 44a to receive a single salient tab 46a. Obturator tip 12a has but a single flexible leg 24a with detent 28a accessible through a single port 38a. All tabs 46 and recesses 50a used for alignment purposes may be eliminated, for example, and replaced by an alignment slot 80, FIG. 6, which is asymmetrical and conformed to receive the asymmetrical shaped legs 24b and 78b so that the tip 12b is automatically properly aligned with shaft 14b. Element 78 which may take any particular form including a shape similar to leg 24a may be provided to keep tip 12a trued up and properly oriented in shaft 14a.

Figure 7:
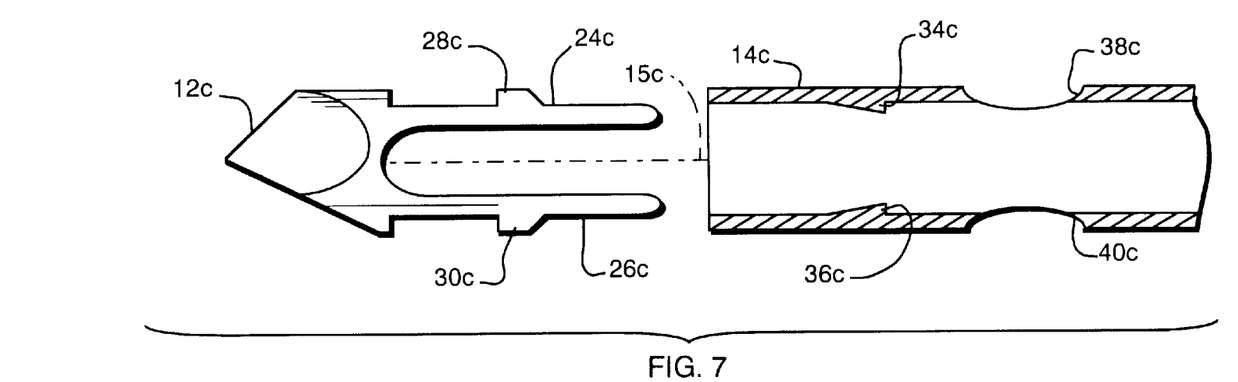
FIG. 7 is an enlarged detailed side elevational view of another embodiment of the removable replaceable tip according to this invention employing two flexible legs with detents for mating with internal stop shoulders on the shaft.

While the stop means thus far have been shown as a part of access ports 38 and 40, this is not a necessary limitation of the invention as they may in fact be constructed as internal stop shoulders 34c, 36c, FIG. 7, which engage detents 28c and 30c on legs 24c and 26c.

Figure 8:
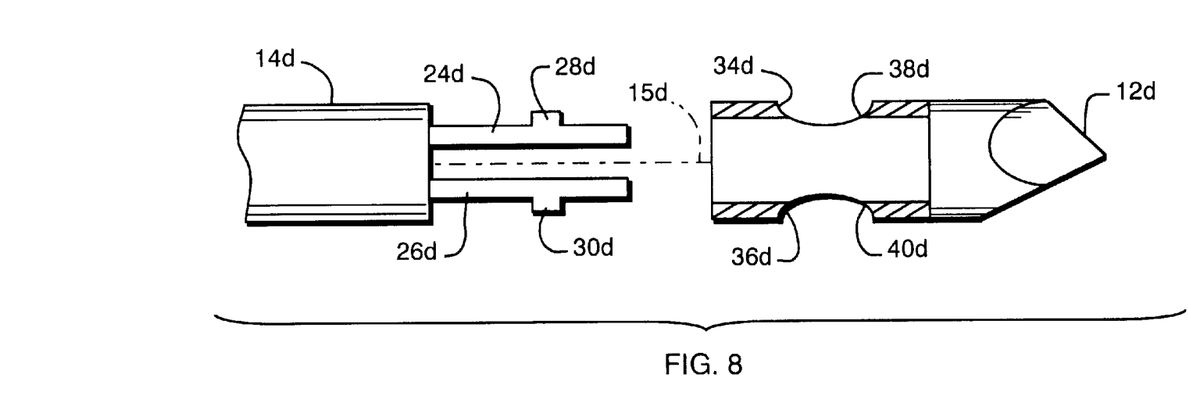
FIG. 8 is a view similar to FIG. 7 of another embodiment of the removable replaceable tip according to this invention in which flexible legs with detents are on the shaft and the tip contains access ports a portion of which function as stop recesses.
Figure 9:
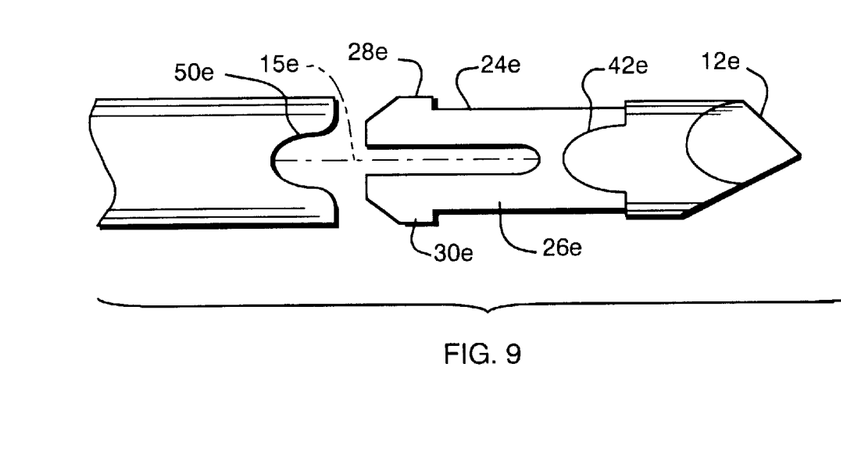
FIG. 9 is a view similar to FIG. 2 in which the alignment means have the salient portion on the tip and the mating recess portion on the shaft.

In addition, although thus far the flexible leg or legs and detents have been shown as a part of the tip and the access ports and stop means have been shown as a part of the shaft, this is not a necessary limitation of the invention as the converse is also contemplated by this invention as shown in FIG. 8, where tip 12d includes access ports 38d and 40d having stop recesses 34d and 36d while shaft 14d contains flexible legs 24d and 26d having detents 28d and 30d. In addition, although the alignment means have been shown with the salient tab on the shaft and the recess on the tip, this is not a necessary limitation of the invention, for as shown in FIG. 9 one or more salient tabs 42e may be provided on tip 12e to self-center and nest in one or more recesses 50e.

Figure 10:
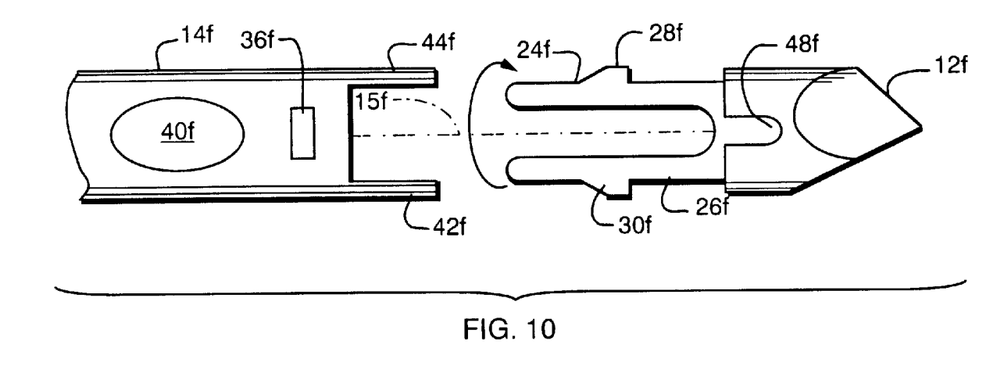
FIG. 10 is a view similar to FIG. 9 of another embodiment of the removable replaceable tip of this invention in which the stop means includes a stop recess separate from the access port.

The access port or ports for reaching flexible legs and compressing them inwardly against their bias may not provide a recessed stop as a part of its configuration. Rather, as shown in FIG. 10, where tip 12f has been rotated 90° with respect to shaft 14f the stop recess 34, 36f has been independently provided to engage detent 28f on leg 24f and a similar stop recess, not shown, is provided on the opposite side of shaft 14f. In FIG. 10, for proper rotational orientation of the tip 12f and shaft 14f, tip 12f must be rotated so that leg 24f comes out of the paper and leg 26f rotates into the paper about the central longitudinal axis 15 so that detent 24 fits into stop recess 36f.

Figure 11:
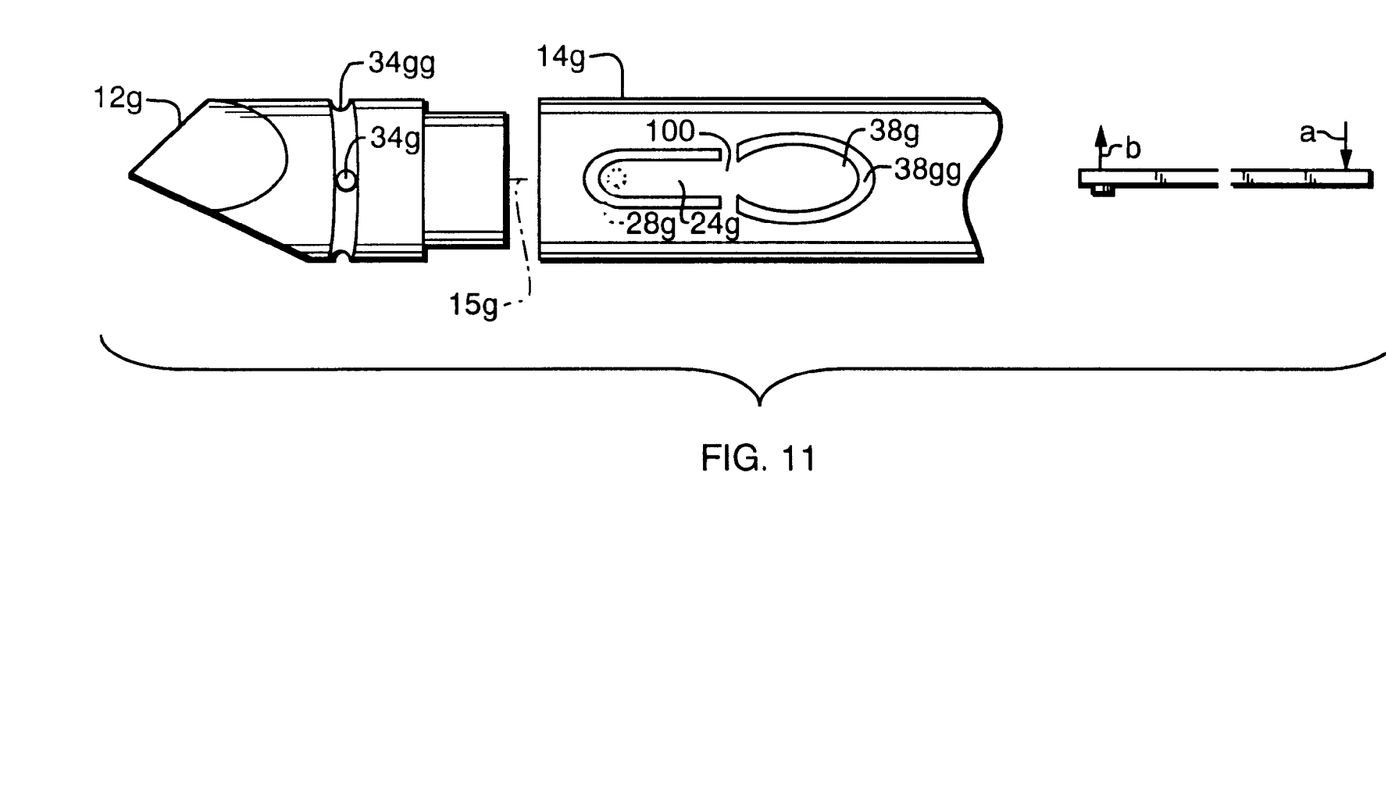
FIG. 11 is a view similar to FIG. 9 of another embodiment of the removable replaceable tip of this invention in which the detent is borne by a flexible leg interconnected with a resilient actuator tab on the shaft and the stop recess is a circumferential groove on the tip.

Although the access means has been shown as one or more ports, this is not a necessary limitation of the invention. For example, as shown in FIG. 11, flexible leg 24g having internally extending detent 28g is flexibly interconnected at junction 100, FIG. 11, with access actuator tab 38g in opening 38gg so that a downward pressure on tab 38g rocks leg 24g upwardly, lifting detent 28g out of stop recess hole 34g. A similar construction may be duplicated on the opposite side of tip 12g and shaft 14g. Hole 34g may be replaced by a circumferential slot 34gg so that orientation is not a problem as detent 28g and a complementary one on the other side of shaft 14g can engage anywhere along groove 34gg.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. An obturator having a removable replaceable tip comprising:

an obturator tip having a sharpened distal end and a first engagement device on its proximal end;

an easily sterilizable tubular, hollow-bodied obturator shaft having a second engagement device on its distal end for lockingly engaging said first engagement device and securing said tip and shaft together;

one of said engagement devices borne by one of said tip and shaft including a flexible member biased to engage the other said engagement device; and toolless access means for enabling the use to directly access and flex, toward the radial center of said shaft, said flexible member against its bias to disengage said engagement devices to release said tip from said shaft, said toolless access means operatively sized and shaped to receive the user's finger such that the user can disengage said engagement devices without using any tools.

2. The obturator of claim 1 further including alignment means for defining orientation of said tip and shaft.

3. The obturator of claim 2 in which said alignment means includes a salient portion on one of said tips and shafts and a mating recess on the other.

4. The obturator of claim 2 in which one of said engagement devices on one of said tip and shaft is asymmetrical in shape and said alignment means includes a conforming guide recess on the other of said tip and shaft for orienting said tip and shaft.

5. The obturator of claim 1 in which said tip includes a circumferential removal groove.

6. The obturator of claim 5 in which said groove has a circular shape.

7. The obturator of claim 5 in which said groove has a polygonal shape.

8. The obturator of claim 1 further including an indicator surface on one of said tip and shaft and a cover member on the other for covering said indicator surface when said tip and shaft are engaged.

9. The obturator of claim 1 in which said indicator surface includes a contrasting colored region.

10. The obturator of claim 1 in which said flexible member snaps said engagement devices together to make an audible indication that said tip and shaft are secured.

11. The obturator of claim 1 in which said tip is made of plastic.

12. The obturator of claim 11 in which said plastic is from the group consisting of polycarbonate, ABS and polysulfone.

13. The obturator of claim 1 in which one of said engagement devices includes at least one flexible leg with a detent and the other engagement device includes a stop for engaging said detent.

14. The obturator of claim 13 in which said stop means is a stop recess for receiving said detent.

15. The obturator of claim 13 in which said stop means is a stop shoulder for abutting said detent.

16. The obturator of claim 13 in which said access means includes a port which allows for manual manipulation of said flexible leg.

17. The obturator of claim 13 in which said stop means includes a peripheral slot.

18. The obturator of claim 1 in which said flexible leg is included on said first engagement device on said tip and said stop means is on said second engagement device on said shaft.

19. The obturator of claim 1 in which said flexible leg is included on said second engagement device on said shaft and said stop means is on said first engagement device on said tip.

20. The obturator of claim 1 in which said access means is on said shaft.

21. The obturator of claim 1 in which said access means is on said tip.

22. An obturator having a removable, replaceable tip comprising:

an obturator tip having a sharpened distal end and a flexible leg extending from the proximal end and having a detent thereon;

an tubular, hollow bodied obturator shaft having stop means for engagement with said detent, said flexible leg being biased to engage said detent with said stop means to secure said tip and shaft; and a toolless access port to enable the user to directly access and flex said leg inward toward the radial center of said shaft to overcome its bias, disengage said detent and stop means and release said tip from said shaft.

23. The obturator of claim 22 in which said stop means includes a stop recess for receiving said detent.

24. The obturator of claim 22 in which said stop means includes a stop shoulder for abutting said detent.

25. The obturator of claim 22 in which said access port is in said shaft and said stop recess forms a part of said port.

26. An obturator having a removable, replaceable tip comprising:

an obturator tip having a sharpened distal end;

an tubular, hollow bodied obturator shaft engaging means for releasably securing said tip and shaft including a flexible leg having a detent on one of said tip and shaft and stop means on the other for engagement with said detent; said flexible leg being biased to engage said detent with said stop means and secure said tip and shaft; and access means for enabling the user to directly access and move said leg inward toward the radial center of said shaft to overcome its bias, disengage said detent and stop means and release said tip from said shaft.

27. The obturator of claim 26 in which said flexible leg is on said tip and said stop means is on said shaft.

28. The obturator of claim 26 in which said flexible leg is on said shaft and said stop means is on said tip.

* * * * *